United States Patent
Norén et al.

(10) Patent No.: US 6,188,928 B1
(45) Date of Patent: Feb. 13, 2001

(54) APPARATUS FOR TISSUE STIMULATION

(75) Inventors: Kjell Norén, Solna; Jakub Hirschberg, Täby; Hans Strandberg, Sundbyberg, all of (SE)

(73) Assignee: Pacesetter AB, Järfälla (SE)

( * ) Notice: Under 35 U.S.C. 154(b), the term of this patent shall be extended for 0 days.

(21) Appl. No.: 09/308,077
(22) PCT Filed: Nov. 3, 1997
(86) PCT No.: PCT/SE97/01830
§ 371 Date: Jul. 22, 1999
§ 102(e) Date: Jul. 22, 1999
(87) PCT Pub. No.: WO98/22183
PCT Pub. Date: May 28, 1998

(30) Foreign Application Priority Data

Nov. 18, 1996 (SE) .................................................... 9604215

(51) Int. Cl.⁷ ...................................................... A61N 1/37
(52) U.S. Cl. ................................................................ 607/28
(58) Field of Search ..................................... 607/9, 13, 28

(56) References Cited

U.S. PATENT DOCUMENTS

| 4,245,643 | * | 1/1981 | Benzing, III et al. ................. 607/28 |
| 4,305,395 | | 12/1981 | Wittkampf et al. . |
| 4,543,956 | | 10/1985 | Herscovici . |
| 5,165,405 | | 11/1992 | Eckwall . |
| 5,330,512 | | 7/1994 | Hauck et al. . |
| 5,417,718 | | 5/1995 | Kleks et al. . |
| 5,431,693 | | 7/1995 | Schroeppel . |
| 5,443,485 | | 8/1995 | Housworth et al. . |
| 5,549,643 | | 8/1996 | Kroll et al. . |
| 5,571,144 | * | 11/1996 | Schroeppel .......................... 607/28 |
| 5,735,883 | * | 4/1998 | Paul et al. ............................. 607/28 |

* cited by examiner

Primary Examiner—William E. Kamm
(74) Attorney, Agent, or Firm—Schiff Hardin & Waite

(57) ABSTRACT

Mathematical functions such as recursive autoregression models which include parameters are used for defining the heart signal and any signals disturbing the heart signal, such as polarization signals. By registering, during a predetermined time interval, the electrode signal for determining the parameters for one or more different mathematical functions, the parameters can be used on their own or in combination to determine the activity of the heart, i.e., whether the registered electrode signal corresponds to a stimulated, spontaneous or absence of heart activity.

13 Claims, 3 Drawing Sheets

APPARATUS FOR TISSUE STIMULATION

BACKGROUND OF THE INVENTION

1. Field of the Invention

The invention relates to an apparatus for tissue stimulation, and in particular a heart pacemaker, for detection of a response to a stimulation pulse when the measured signal is corrupted by an electrode polarisation artefact.

2. Description of the Prior Art

It is desirable that pacemakers have a low energy consumption such that the battery lasts longer. To enable the reduction of the energy consumption it must be clear whether there has been a capture (=a heart contraction/ evoked response) or not at the prevailing stimulation voltage. For a proper detection of capture, it is important that the artefact at stimulation, i.e. the polarization voltage, is not so large that it is detected as capture. If the polarization voltage could be eliminated the detection of capture would be easier and more reliable.

U.S. Pat. No. 4,543,956 discloses a system for detecting the evoked response in which the polarization is neutralized using a biphasic waveform technique whereby a compensating current pulse is transmitted in the opposite direction from the stimulating current pulse. However, the compensating current pulse is often emitted very close in time to the stimulation pulse, the recharge pulse thus tending to mask the electrical response from the heart and in particular in the case where a unipolar electrode is used.

U.S. Pat. No. 5,431,693 discloses a pacemaker for detecting capture based on the observation that the non-capture potential is exponential in form and the evoked response potential, while generally exponential in form, has one or more small-amplitude perturbations superimposed on the exponential waveform and whereby the perturbations are enhanced for ease of detection. The perturbations involve relatively abrupt slope changes, which are enhanced by processing the waveform signal differentiation. Abrupt slope changes in the second derivative are used to detect morphological features indicative of capture which are otherwise difficult to discriminate.

U.S. Pat. No. 5,165,405 relates to a pacemaker comprising means for acquiring the curve of the polarisation phenomenon by stimulating the tissue with a stimulation energy lying below the stimulation threshold, so that the electrical potential signal in the tissue subsequently acquired by the detector means corresponds to the polarization phenomena produced by the stimulation attempt without these having an evoked response of the tissue superimposed thereon. By regularly updating the polarisation signal, an optimal compensation of the polarisation components contained in the acquired electrical potential signal is achieved for the purpose of detecting an evoked response.

U.S. Pat. No. 5,417,718 defines a pacemaker that includes a so called Autocapture™ system for automatically maintaining the energy of the stimulation pulses generated by the pacemaker at a predetermined level safely above that needed to effectuate capture. The Autocapture™ system performs its function by comparing the electrical evoked response of the heart following the generation of a stimulation pulse to a polarization template determined by a capture verification test. During the capture verification test, the Autocapture™ system causes the pacemaker to first generate a series of pacing pulse pairs. The first pulse of the pair has a high energy to ensure capture. The second pulse of the pair is of the prescribed stimulation energy. The signal corresponding to the second pulse (which signal is dominated by polarization information) is sensed through a sensing circuit having a specified sensitivity setting. Such signal is stored as the polarization template corresponding to that particular energy and sensitivity setting. In view of the lead polarization signal not being easily characterised, due to it being a complex function of e.g. the lead materials, lead geometry, tissue impedance, stimulation energy, most of which are continuously changing over time, the capture verification test creates a table of polarization templates as a function of sensitivity settings for a particular stimulation energy.

SUMMARY OF THE INVENTION

It is an object of the invention to provide an apparatus for tissue stimulation wherein the reaction of the tissue to the stimulation is reliably detected independently of the presence of a polarization voltage.

The invention is embodied in an apparatus for tissue stimulation achieving a reliable capture detection which would make it possible to use different pacemakers with one and the same electrode, and in particular a unipolar electrode. This would be highly favorable for patients who have an already implanted and well functioning unipolar electrode, but who are in need of a new pulse generator due to e.g. battery end of life (EOL) and/or in need of a more modern pacemaker e.g. comprising the Autocapture™ function.

Due to a faster detector unit response, another advantage would be the possibility of more reliably reducing the stimulation voltage needed for capture (Autocapture™ function).

These advantages are achieved in accordance with the invention, which is based on the observation that a detected heart signal and any signal disturbing the detected heart signal, e.g. a polarisation signal, can be approximated by mathematical functions. These functions comprise parameters. These parameters are different for each of these mathematical functions depending on if the stimulation pulse has caused capture or not. By letting the pacemaker during a predetermined time interval register the electrode signal for determining the parameters for one or more different mathematical functions, one or several parameters can be used to determine the activity of the heart, i.e. if the registered electrode signal corresponds to capture or non capture.

In a preferred embodiment the mathematical functions may be more or less direct or indirect and hence, an autocorrelation calculation may be needed before the determination of the parameters. A regression analysis may also be appropriate. Moreover, by using a recursive autoregression model the parameters for the detected signal with respect to the corresponding stimulation pulse may be used as a means for detecting the evoked response. Furthermore, a Kalman filter may be used to determine the parameters, especially if the signals have properties known beforehand.

In a preferred embodiment the parameters are continuously determined during a time interval of 10 ms to 120 ms after a stimulation pulse and evaluated in a window from 15 ms to 120 ms or 50 to 100 ms. In another preferred embodiment the parameters are determined and evaluated only once at a point between 50 and 100 ms and preferably at 60 ms after the stimulation pulse.

DESCRIPTION OF THE DRAWINGS

FIG. 2C shows the combined measured signal of evoked response and polarization of FIG. 2A and FIG. 2B, respectively, according to an embodiment of the invention.

DESCRIPTION OF THE PREFERRED EMBODIMENTS

Figure 1:
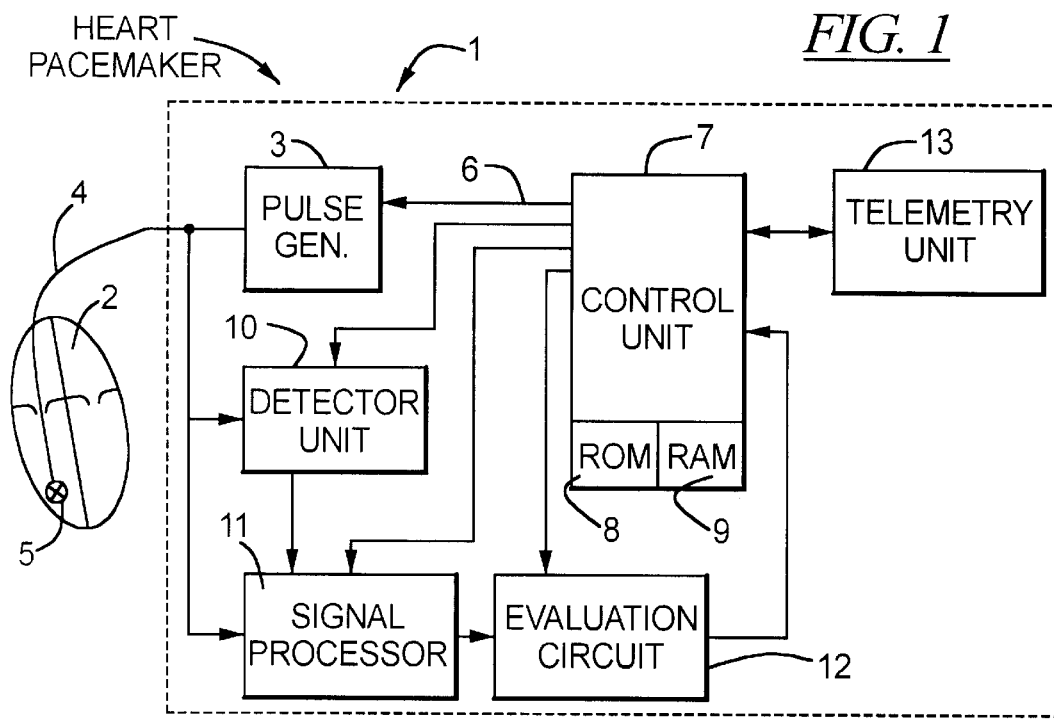
FIG. 1 is a schematic block diagram of an apparatus for tissue stimulation, in the form of a hear pacemaker, consturcted in accordance with the principles of the present invention.

As a preferred embodiment of the device of the invention, FIG. 1 shows the block circuit diagram of a heart pacemaker 1 for tissue stimulation, in this case the stimulation of a heart 2. The heart pacemaker 1 includes a stimulation pulse generator 3 that has its output side connected via an electrode line 4 to an electrode 5 applied in the ventricle of the heart 2 for stimulating the heart 2 with stimulation pulses. Of course, even if the preferred embodiment shows the electrode to be located in the ventricle, the invention also covers the electrode being located in the atrium. The stimulation pulse generator 3 can be activated to deliver a stimulation pulse via a control line 6, which is connected to a corresponding output of a control unit 7. The stimulation pulse generated by the stimulation pulse generator 3 may be anyone of the stimulation pulses known to the skilled person. The duration of the respective stimulation pulse as well as the setting of the amplitude setting of the stimulation pulses may also be set via the same line 6. In the illustrated preferred embodiment, the control unit 7 is a microprocessor to which a read-only memory (ROM) 8 and a random access memory (RAM) 9 are assigned, these being connected to the microprocessor 7 via data lines, address lines, as well as via a write-read switching line in the case of the random memory 9. A program that executes all functions of the heart pacemaker 1 via the microprocessor 7 is stored in the read-only memory 8. Therein mathematical functions approximating the heart signal and any signal disturbing the heart signal, e.g. polarization signals, are stored to be used by the control unit 7 for determining and evaluating if a detected signal corresponds to stimulated, spontaneous or lack of activity of the heart.

The heart signal may be approximated by the mathematical functions $$A/(t-D)$$

where A and D are parameters or $$C*t/(E+t^2)$$

where C and E are parameters.

A polarization signal may be approximated by the mathematical function $$B*exp(-t/T)$$

where B and T are parameters in accordance with the results of the Master Thesis at the Royal Institute of Technology, Stockholm, with the title "A Model of the Polarisation Dependent Impedance" by Åsa Uhrenius, published December 1995.

Yet another mathematical function may be a recursive autoregression model. In an ideal situation the parameters are constants for the whole period of the detected signal. However, due to the signal only being detected during a predetermined time interval and for a limited quantity of data, the parameters are substantially constant during the predetermined time interval, i.e. the parameters are to a certain degree time-dependent.

The pacemaker 1 also includes a telemetry unit 13 connected to the microprocessor 7 for programming and for monitoring functions of the pacemaker 1 on the basis of data exchange with an external programming and monitoring device (not shown).

By means of the telemetry unit 13 the parameters of the mathematical functions are preferably determined at the implantation so that they are adapted to the patient and thereafter stored in the ROM 8. The mathematical functions may also be chosen and stored in the ROM 8 by means of the telemetry unit 13 at implantation or they may be stored at the time of fabrication of the pacemaker 1.

In order to be able to acquire the reaction of the heart, e.g. given a stimulation, the heart pacemaker 1 contains a detector unit 10 which has an input side connected via the electrode line 4 to the electrode 5 for acquiring the electrical potential in the heart tissue. This arrangement is simple because only a single electrode 5 is required both for stimulating the heart 2 and for acquiring the reaction thereof. However, because the tissue is so highly polarized in the immediate region of the electrode 5 after every stimulation, the polarization voltage may superimpose the evoked response of the heart 2 to the degree of making it unrecognizable. Of course, another preferred embodiment of the device of FIG. 1 also allows the employment of a separate stimulation electrode and measuring electrode for respectively stimulating the tissue and for acquiring the evoked response.

The curve of the electrical potential in the heart tissue acquired by the detector unit 10 and corresponding to electrical heart activity is supplied to an input of a signal processor 11. The signal processor 11 acquires a quantity of data corresponding to the curve of the electrical potential in the heart tissue detected by the detector unit 10. The signal processor 11 may contain means for pre-processing the by the detector unit 11 detected signal, e.g. means for band-pass filtering the detected signal. Thereafter the parameters are determined before the parameters are sent to the evaluation circuit 12. The parameters may after the quantity of data has been acquired be determined either only once before being sent to the evaluation circuit 12 or they may be determined continuously during the predetermined time interval during which the quantity of data is acquired and consequently, the more data acquired the more reliable the determination of the parameters.

The processing of the signal and evaluation of parameter values may be performed as mentioned below:

The signal from the electrodes is amplified and band pass filtered before further processing. Such a bandpass filter should not influence signals that are sought for further means a high pass filter should be used having a frequency limit in the order of 3–0.1 Hz to avoid DC-level or very slow changing signals. A low pass limitation to attenuate high frequency interference may have a frequency limit in the order of 1000–200 Hz.

The filtered signal is quantified in an analog to digital (AD) converter using a sampling rate in the order of 200–800 samples/second. The values are stored in the RAM 9. The stored values are then utilized in a computing process to determine the parameter values characterizing an idealized signal, the idealized signal being constructed from simple mathematical functions as mentioned above. The parameter values belonging to the idealized function are determined so that there is a best adaptation or least error compared to the real measured signal.

The computed parameter values are used to discriminate between capture and non capture. If one or several parameter values are within some predetermined limits, then this is used as an indicator of capture. The opposite is also valid. These limits are determined at the time of implantation.

If the quantity of stored values is equal to the quantity of parameters for each function the parameter values can be determined by solving an equation system. For example, the function $A/(t-D)$ requires two data points $Z_1$ and $Z_2$ measured at time points $t_1$ and $t_2$ after stimulation to determine the two parameters A and D.

There is always a small influence from interfering sources, measurement accuracy, etc. which may give inaccurate determination of the parameters. Therefore a longer sequence of measured values is preferably used. The parameters can then not be solved from a simple equation system. There are several methods to solve so called over estimated equations where the quantity of known values exceeds the quantity of unknown. There are matrix methods, which require some computing.

A suitable method is iterative solving, whereby the difference is minimized between the measured values and the values of the idealised function.

The function F gives values $F_i$ at time points $t_i$ for a given parameter set. $Z_i$ are the measured values at corresponding time points. In the least squares method the "error" function with the "error" value E is determined: $E = \sum_{1:N}(F_i - Z_i)^2$.

Then one or some of the parameter values are changed with small steps and the "error" function is determined again. Thereby one has the possibility to get the parameter values through iterative steps that minimize the error value. The sought parameter values are those determined by iteration and consequently they will be used for indication of heart occurrence.

During iteration a simplified requirement may be to stop the computing when the error is below a predetermined limit instead of totally eliminating the error value.

Another simplification that may be used is a simpler error function: $E = \sum_{1:N}(|F_i - Z_i|)$, where $|F_i - Z_i|$ means the absolute value of Fi–Zi. Then must be used to avoid other problems resulting from noise, special shape of the signals, etc. Problems arising during computation may be reduced by averaging, value limitations, etc.

To bring down the number of iterations it is essential to have properly predetermined starting values of the parameters, to have a suitable step size when varying the parameters and to have good stop criteria for the iterations.

The least squares method is well known to the person skilled in the art.

By means of the Kalman filter the determination of the parameters is faster and more reliable, since known properties of the heart signals and signals disturbing the heart signals are used. The Kalman filter is a mathematical process whereby properties which were known before the measurement was started are taken into account. It is especially suitable if the registered information, to be taken into account together with the properties known beforehand, is limited or badly determined. In this case, either the general appearance of the heart signal or the polarisation signal are known beforehand or they may be determined by repeated registration. Hence, it is known what the preferred parameters should be for capture and non capture. The parameter's distribution is used together with the Kalman filter so as to more reliably determine the parameters for the latest registered signal and thereafter letting the evaluation circuit 12 decide if capture or non capture activity or lack of activity prevails based on the value of one or more parameters.

The parameters as a function of time will then characterise the measured detected signal corresponding to stimulated, spontaneous or lack of heart activity 1. There will be significant differences between the parameters as a function of time if the polarisation signal is present in the detected signal, as can clearly be seen from FIGS. 3 and 4.

Less advanced algorithms for estimating the parameters of the mathematical function, e.g. a recursive autoregression model, may be used, e.g. the least square method. The Kalman filter algorithm as well as other less advanced algorithms, which are used for determining the parameters defining the mathematical functions, are well known in the art of signal processing. However, until now these algorithms have not been used in the field of pacemaker technology, and in particular not for reliably detecting capture.

The identified parameters as a function of time are then fed to an evaluation circuit 12 wherein a logical signal capture/no capture is generated by evaluating the parameters as a function of time after the end of the stimulation pulse. The parameters are preferably evaluated by comparing them to predetermined parameters that have been determined at implantation for the particular mathematical functions stored in the ROM 8 for defining the heart signal and any signal disturbing the heart signal. The evaluation circuit 12 need not be further described, since it would be well-known to the skilled person how to build such a circuit. However, it may be build of conventional linear processing circuits combined with threshold detection and logical circuits.

Depending on the electrode placement and on the type of electrode used, unipolar or bipolar electrode, the heart response to a stimulation pulse arrives after 2 to 15 ms and 20 to 40 ms respectively. In a preferred embodiment the parameters are continuously determined during a time interval of 10 ms to 120 ms after a stimulation pulse and evaluated in a window from 15 ms to 120 ms or 50 to 100 ms. In another preferred embodiment the parameters are determined and evaluated only once at a point between 50 and 100 ms and preferably at 60 ms after the stimulation pulse.

Figure 4A:
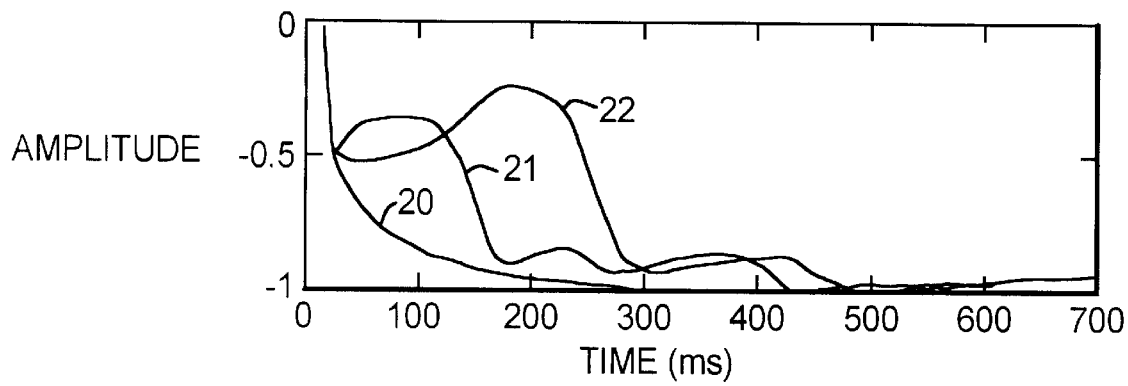
FIG. 4A shows the normalized first parameter for the three different signals in FIGS. 2A through 2C, according to an embodiment of the invention.
Figure 4B:
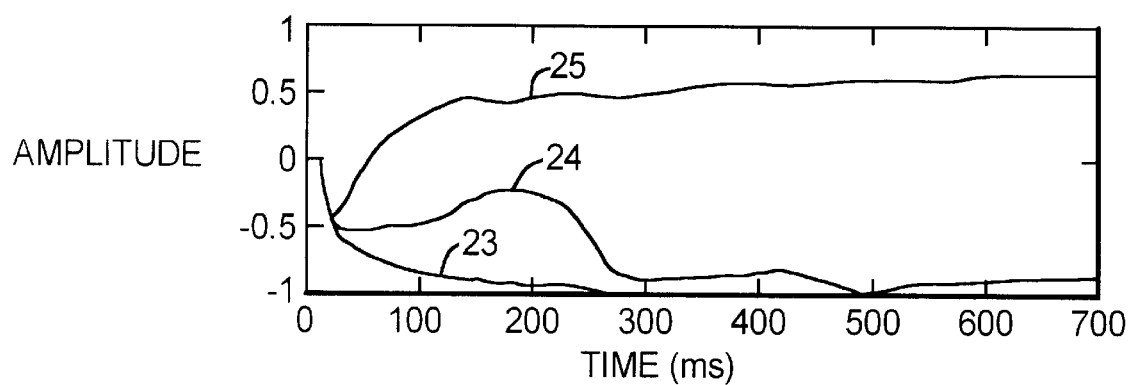
FIG. 4B shows the second normalized parameter for the three different signals in FIGS. 3A through 3C, according to an embodiment of the invention.

Experiments have shown that the parameters are more or less equal up to the break point of 30 ms, which can be seen from FIGS. 4A and 4B, thus indicating that it is preferable to determine the parameters as a function of time starting 15 ms after the end of the stimulation pulse. However, detection may start at 30 ms after the end of the stimulation pulse. The resulting logical signal capture/no capture from the evaluating circuit 12 is an output corresponding to a, by the control unit 7 for the detector unit 10, pre-selected detection window.

The detector unit 10, the signal processor 11 and the evaluation circuit 12 may be activated via control lines respectively, which are connected to a corresponding output of the control unit 7. Of course, the preferred embodiment of the device as shown in FIG. 1 also allows the microprocessor 7 to perform the functions of the detector unit 10, the signal processor 11, and the evaluation circuit 12.

Figure 2A:
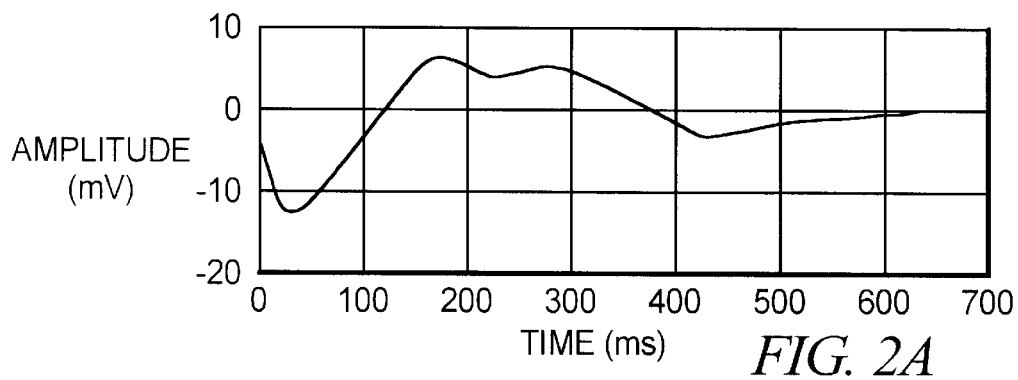
FIG. 2A shows a unipolar evoke response measured between the tip in a ventricle and a pacemaker can, according to an embodiment of the invention.
Figure 2B:
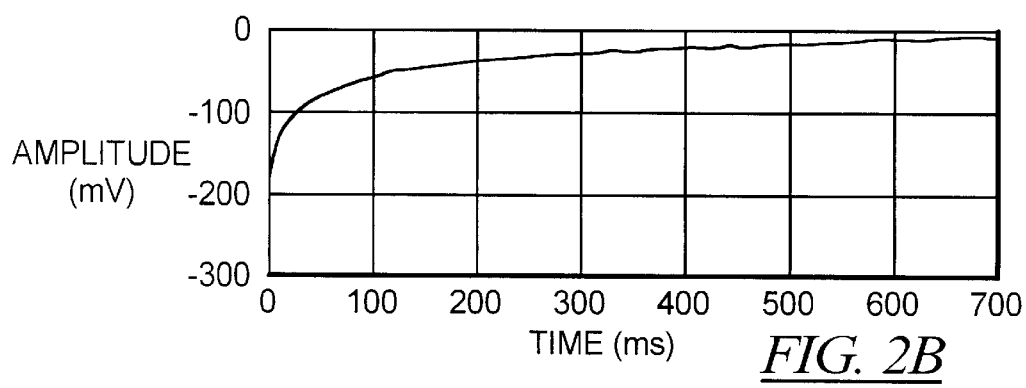
FIG. 2B shows the polarization modeled by three exponential decays, a constant negative level and a positive linear trend according to an embodiment of the invention.
Figure 2A:
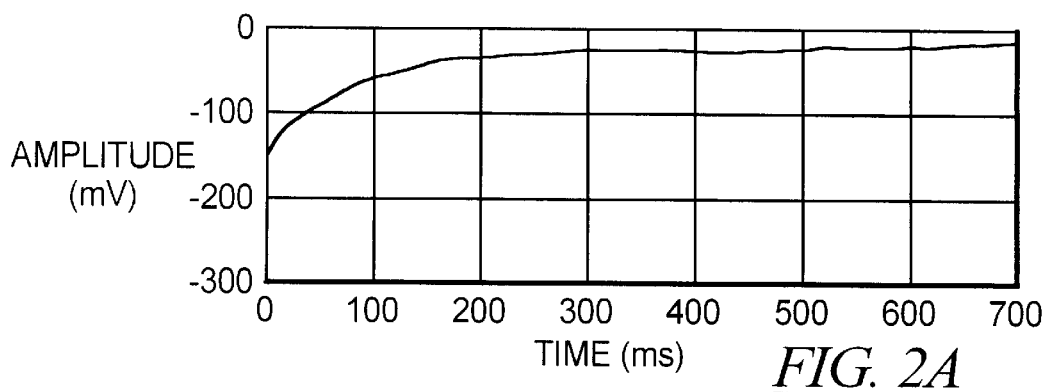

FIGS. 2 to 4 show an example of how the three different possible signals of FIGS. 2A, 2B and 2C are distinguished from each other by determining the time-dependent parameters of a mathematical function such as a recursive autoregression model using a Kalman filter.

FIGS. 2A, 2B and 2C show respectively a unipolar evoked response measured between the tip in a ventricle and a pacemaker can, the polarization modelled by three exponential decays, a constant negative level and a positive linear trend, and the combined measured signal of evoked response and polarization of FIG. 2A and FIG. 2B respectively. As is clear from FIG. 2B and FIG. 2C it is quite difficult to distinguish the combined signal of evoked response and polarization from the pure polarization signal.

FIGS. 3 and 4 show an example using two time-dependent parameters for characterising the signals. The proposed predetermined model is a recursive autoregression model and the parameters thereof are determined using the Kalman filter algorithm. As already mentioned, less advanced algorithms may be used. Furthermore, one parameter or more may be used for best defining the recursive autoregression model. However, two to four parameters are preferred for optimising the reliability of the model and the time needed for determining the parameters, since the faster and the more reliable logical signal capture/no capture is determined, the faster and the more reliable the control unit 7 can adapt the control signals to the stimulation pulse generator 3 to the prevailing situation. So as to obtain a reliable result, the signal processor 11 preferably samples the curve obtained with the detector unit 10 at a rate of 1000 Hz.

Figure 3A:
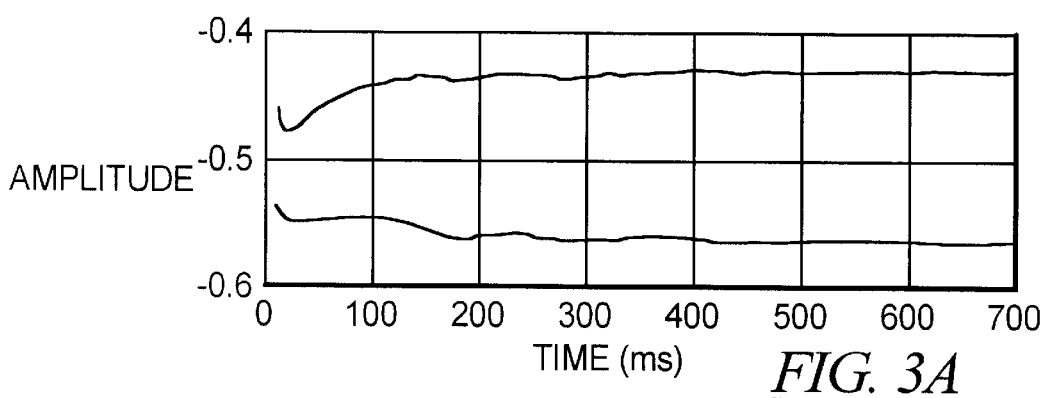
FIG. 3A shows two parameters as a function of time calculated using a Kalman filter algorithm and the signal from FIG. 2A, according to an embodiment of the invention.
Figure 3B:
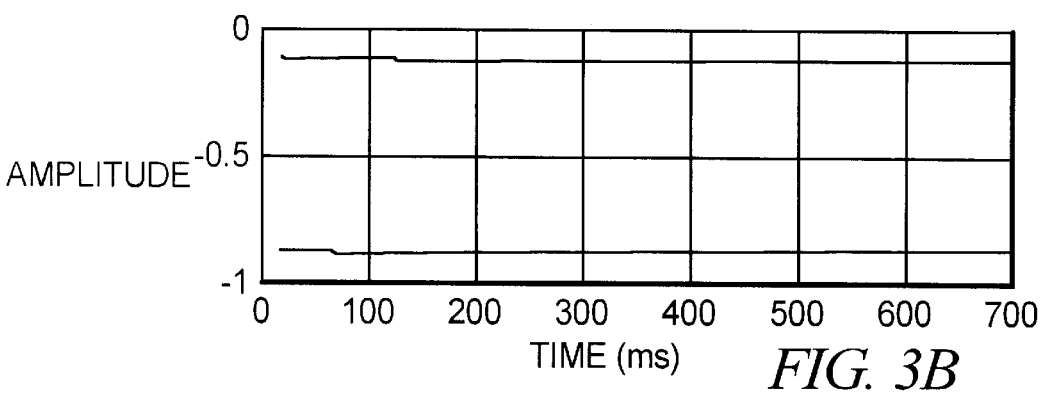
FIG. 3B shows two parameters as a function of time calculated using a Kalman filter algorithm and the signal from FIG. 2B, according to an embodiment of the invention.
Figure 3C:
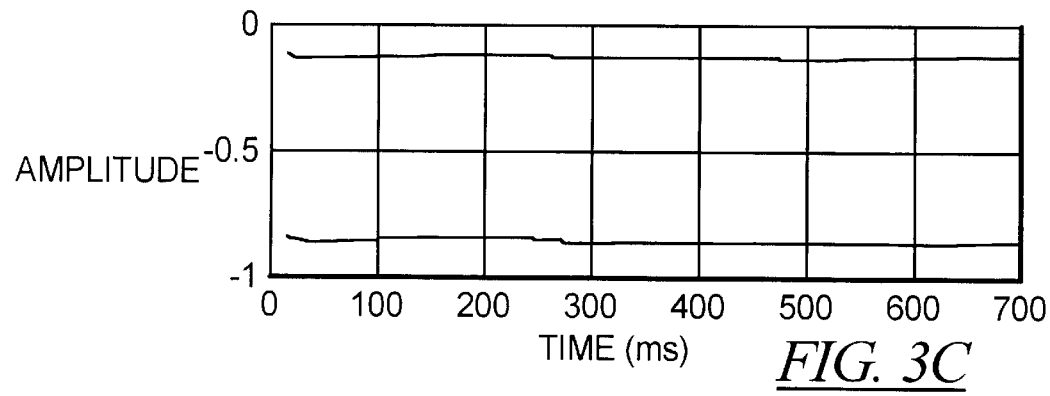
FIG. 3C shows two parameters as a function of time calculated using a Kalman filter algorithm and the signal from FIG. 2C, according to an embodiment of the invention.

FIGS. 3A, 3B and 3C thus show the three pairs of parameters obtained from the three signals by using the proposed model. The only pre-processing was to remove the average level from the combined measured signal.

It is also possible to normalize the parameters to a peak-to-peak value of one unit and let the time-dependent parameters start at zero at the beginning of a predefined detection window. FIGS. 4A and 4B show the normalised first and second parameters for the three different signals in FIG. 2A to 2C, the detection window being defined to start 15 ms after the end of the stimulation pulse. At the time of 200 ms, in FIG. 4A the curves are from bottom to top: polarisation only 20, evoked response only 21, and combined measured signal 22; and in FIG. 4B: polarisation only 23, combined measured signal 24, and evoked response only 25. From FIGS. 4A and 4B it is clear that since the signals are substantially equal until 30 ms, the evaluation circuit 12 may be activated shortly before the break point 30 ms for determining the logical signal capture/no capture.

In the example shown in FIGS. 2 to 4, the signal processing is started immediately after the stimulation pulse at time=0 and continued over a long period of time. A preferred signal processing window would be in the time interval of 20 ms to 120 ms after the end of the stimulation pulse. The evaluation window of the evaluation circuit 12 may be a window inside the signal processing window or equal to it, e.g. 25 ms to 120 ms after the stimulation pulse. However, the signal processing may also be started at 60 ms after the end of the stimulation pulse.

One skilled in the art will appreciate that the present invention can be practised by other than the described embodiments, which are presented for purposes of illustration, and the present invention is limited only by the claims which follow.

We claim as our invention:

1. An apparatus for tissue stimulation comprising a pulse generator which generates stimulation pulses, an electrode connected to said pulse generator and adapted for delivering said stimulation pulses in vivo to tissue, a detector which acquires an electrical signal corresponding to an electrical potential at said tissue during a predetermined time interval following a delivered stimulation pulse, a determination unit which determines a value of at least one parameter of a predetermined mathematical function, which produces a best adaptation of said predetermined mathematical function to said electrical signal during said predetermined time interval, and an evaluation unit which compares the at least one parameter with a predetermined corresponding parameter range and which generates a signal indicative of a result of said comparison.

2. An apparatus as claimed in claim 1, wherein said mathematical function is $$A/(t-D)$$

where A and D are parameters and t is time.

3. An apparatus as claimed in claim 2 wherein said determination unit determines the parameters using two data points of said electrical signal.

4. An apparatus as claimed in claim 1, wherein said mathematical function is $$C*t/(E+t^2)$$

where C and E are parameters and t is time.

5. An apparatus as claimed in claim 1, wherein said electrical signal is a polarization signal and wherein said mathematical function is $B*\exp(-t/T)$ where B and T are parameters and t is time.

6. An apparatus as claimed in claim 5 wherein said determination unit continuously determines the parameter during a time interval of 10 ms to 120 ms after a stimulation pulse.

7. An apparatus as claimed in claim 6, wherein said evaluation unit evaluates said at least one parameter only once at a point between 50 and 100 ms after the stimulation pulse.

8. An apparatus as claimed in claim 7, wherein said evaluation unit evaluates said at least one parameter at 60 ms after the stimulation pulse.

9. An apparatus as claimed in claim 6, wherein said evaluation unit evaluates said at least one parameter during at time window from 15 ms to 120 ms after the stimulation pulse.

10. An apparatus as claimed in claim 1, wherein said mathematical function is a recursive autoregression model.

11. An apparatus as claimed in claim 1 wherein said determination unit determines said at least one parameter using the last squares method.

12. An apparatus as claimed in claim 1 wherein said determination unit determines said at least one parameter using a Kalman filter.

13. An apparatus as claimed in claim 1 wherein said signal generated by said evaluation unit indicates capture if said at least one parameter falls within said corresponding parameter range, and indicates non-capture if said at least one parameter does not fall within said corresponding parameter range.

* * * * *